(12) United States Patent
Messerli

(10) Patent No.: US 12,740,817 B2
(45) **Date of Patent: *Sep. 22, 2026**

(54) TRANSVERSELY DISPLACING STRUCTURES IN THE BODY

(71) Applicant: Lenoss Medical, Inc., Bristol, RI (US)

(72) Inventor: Dom Messerli, Bristol, RI (US)

(73) Assignee: Lenoss Medical, Inc., Bristol, RI (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/677,108

(22) Filed: May 29, 2024

(65) Prior Publication Data

US 2025/0099150 A1 Mar. 27, 2025

Related U.S. Application Data

(63) Continuation of application No. 17/306,636, filed on May 3, 2021, now Pat. No. 12,029,463, which is a continuation of application No. 16/022,202, filed on Jun. 28, 2018, now Pat. No. 10,993,756.

(60) Provisional application No. 62/647,356, filed on Mar. 23, 2018.

(51) Int. Cl.
*A61B 17/88* (2006.01)
*A61B 17/00* (2006.01)

(52) U.S. Cl.
CPC .................... *A61B 17/8858* (2013.01); *A61B 2017/00367* (2013.01); *A61B 2017/0042* (2013.01); *A61B 2017/00862* (2013.01)

(58) Field of Classification Search
CPC ..... A61B 17/88; A61B 17/8858; A61B 17/16; A61B 17/1617; A61B 17/1637
See application file for complete search history.

(56) References Cited

U.S. PATENT DOCUMENTS

| | | | |
|---|---|---|---|
| 2,556,783 | A | 6/1951 | Wallace |
| 2,649,092 | A | 8/1953 | Wallace |
| 3,517,128 | A | 6/1970 | Hines |
| 3,713,447 | A | 1/1973 | Adair |

(Continued)

OTHER PUBLICATIONS

[No Author Listed] "Spider Kyphoplasty and Vertebroplasty System", Sintea-Plustek, Jul. 20, 2011, 2 pages.

(Continued)

*Primary Examiner* — Christopher J Beccia
(74) *Attorney, Agent, or Firm* — Fish & Richardson P.C.

(57) ABSTRACT

System and methods for transversely displacing structures in the body can include a device for displacing structures in a patient's body, the device having: a handle; a first longitudinal member fixed in position relative to the handle; a second longitudinal member coaxial with the first longitudinal member, the second longitudinal member movable relative to the first longitudinal member between a retracted position and an extended position; and at least one resilient blade extending from a proximal end to a distal end, the proximal end of the at least one resilient blade mechanically fixed in position relative to the second longitudinal member; wherein the distal end of the at least one resilient blade is engaged with the first longitudinal member when the second longitudinal member is in its extended position and disengaged from the first longitudinal member when the second longitudinal member is in its retracted position.

20 Claims, 11 Drawing Sheets

(56) References Cited

U.S. PATENT DOCUMENTS

| | | | | |
|---|---|---|---|---|
| 3,799,172 | A | 3/1974 | Szpur | |
| 4,808,163 | A | 2/1989 | Laub | |
| 5,275,610 | A | 1/1994 | Ederbach | |
| 5,454,365 | A | 10/1995 | Bonutti | |
| 5,554,101 | A * | 9/1996 | Matula | A61B 17/0218 600/219 |
| 5,678,572 | A | 10/1997 | Shaw et al. | |
| 6,676,665 | B2 | 1/2004 | Foley et al. | |
| 6,679,886 | B2 | 1/2004 | Weikel et al. | |
| 6,849,080 | B2 | 2/2005 | Lee et al. | |
| 7,044,954 | B2 | 5/2006 | Reiley et al. | |
| 7,114,501 | B2 | 10/2006 | Johnson et al. | |
| 7,641,664 | B2 * | 1/2010 | Pagano | A61B 17/8858 606/92 |
| 7,722,612 | B2 | 5/2010 | Sala et al. | |
| 7,815,643 | B2 | 10/2010 | Johnson et al. | |
| 8,353,911 | B2 | 1/2013 | Goldin | |
| 8,486,082 | B2 | 7/2013 | Geisert | |
| 10,219,851 | B1 | 3/2019 | Messerli | |
| 10,993,756 | B2 * | 5/2021 | Messerli | A61B 17/8858 |
| 12,029,463 | B2 | 7/2024 | Messerli | |
| 2002/0026197 | A1 * | 2/2002 | Foley | A61B 17/8858 606/105 |
| 2004/0059338 | A1 | 3/2004 | Ebner | |
| 2005/0070911 | A1 | 3/2005 | Carrison et al. | |
| 2005/0182417 | A1 | 8/2005 | Pagano | |
| 2008/0300636 | A1 | 12/2008 | Carli et al. | |
| 2009/0005821 | A1 | 1/2009 | Chirico et al. | |
| 2019/0290345 | A1 | 9/2019 | Messerli | |
| 2022/0087728 | A1 | 3/2022 | Messerli | |

OTHER PUBLICATIONS

[No Author Listed] "Xvoid Cavity Creation System", Stryker, 1 page.

Extended European Search Report in European Appln. No. 23177487.8, mailed on Jan. 30, 2024, 11 pages.

International Preliminary Report on Patentability in International Appln. No. PCT/US2019/022862, mailed on Oct. 8, 2020, 9 pages.

International Search Report and Written Opinion in International Appln. No. PCT/US2019/022862, mailed on Jul. 2, 2019, 17 pages.

Kim et al., "Sunflower Kyphoplasty: A New Restoration Method for Vertebral Compression Fracture," Korean J Pain, Nov. 2004, 17(2):166-169 (with English abstract).

Office Action in Canadian Appln. No. 3,094,800, mailed on May 21, 2025, 4 pages.

Office Action in U.S. Appl. No. 12/068,799 mailed on Jan. 19, 2011, 10 pages.

*Orthophoenix LLC*, v. *Sintea Plustek LLC*; John and/or Jane Does 1-100, "Orthophoenix's Complaint for Patent Infringement," Case [Unassigned], filed on Jun. 4, 2013, 23 pages.

Preliminary Amendment in US20080300636, dated Feb. 12, 2008, 7 pages.

Spineart.com [online], "Tektona Vertebral Fragment Reduction," retrieved on Mar. 31, 2025, retrieved from URL <http://spineart.com/product-platforms/trauma/7/product/tektona%C2%AE/689>, 1 page.

* cited by examiner 140
114

141
140
114

141
142
112

144
116
148
110
146
150
118

149
152

158
158

TRANSVERSELY DISPLACING STRUCTURES IN THE BODY

CROSS-REFERENCE TO RELATED APPLICATIONS

This application is a continuation application of and claims priority to Ser. No. 17/306,636, filed on May 3, 2021, which is a continuation application of and claims priority to U.S. application Ser. No. 16/022,202, filed on Jun. 28, 2018, now U.S. Pat. No. 10,993,756, which claims priority to U.S. Provisional Application No. 62/647,356, filed on Mar. 23, 2018, the disclosure of each application is hereby incorporated thereto.

FIELD

This disclosure relates generally to surgical instrumentation and methods for transversely displacing structures in the body such as, for example, surgical instrumentation and methods for transversely displacing structures associated with the spine.

BACKGROUND

There are medical treatments that include transversely displacing structures in the body. For example, kyphoplasty is a procedure used to treat painful vertebral compression fractures in the spinal column, which are a common result of osteoporosis. Doctors displace portions of the fractured bone to create a space and then fill the space with cement or another filler.

SUMMARY

This disclosure describes surgical instrumentation and methods for transversely displacing structures in the body.

Some devices for creating a cavity during spinal surgery include: an inner body with a first end and a second end; an outer sleeve coaxial with the inner body, the outer sleeve movable relative to the inner body between a retracted position and an extended position; a trigger mechanism connected to the outer sleeve and configured to apply an axial force to the outer sleeve; a first strip of resilient material having a first end and a second end, the first end of the first strip of resilient material fixed in position relative to the outer sleeve; and a second strip of resilient material having a first end and a second end, the first end of the second strip of resilient material fixed in position relative to the outer sleeve; wherein the second ends of the first strip of resilient material and the second strip of resilient material are releasably engaged with the inner body when the outer sleeve is in its extended position and disengaged from the inner body when the outer sleeve is in its retracted position.

Some devices for displacing structures in a patient's body include: an inner body having a first end and a second end; an outer sleeve coaxial with the inner body, the outer sleeve movable relative to the inner body between a retracted position and an extended position; and a strip of resilient material having a first end and a second end, the first end of the strip of resilient material fixed in position relative to the outer sleeve; wherein the second end of the strip of resilient material is releasably engaged with the inner body when the outer sleeve is in its extended position and disengaged from the inner body when the outer sleeve is in its retracted position.

Embodiments of these devices can include one or more of the following features.

In some embodiments, the second end of the inner body defines a cavity that is aligned with the first strip of resilient material when the outer sleeve is in its retracted position. In some cases, the second end of the first resilient strip is outside the cavity when the outer sleeve is in its retracted position. In some cases, the cavity extends from a first opening oriented towards the first resilient strip to a second opening oriented away from the resilient strip. In some cases, a central portion of the first resilient strip is spaced apart from the inner body when the outer sleeve is in its extended position and the second end of the strip of resilient material is disposed in the cavity. In some cases, the second end of the first strip of resilient material has a tapered shape.

In some embodiments, devices also include a handle with a trigger, the trigger mechanically connected to the outer sleeve such that operation of the trigger moves the outer sleeve relative to the handle. In some cases, the second end of the inner body is fixed in position relative to the handle.

In some embodiments, a portion of the inner body defines a slot positioned within the outer sleeve. In some cases, devices also include a connector extending through the slot, the connector attached to the outer sleeve and the first strip of resilient material and fixed in position relative to the outer sleeve and the strip of resilient material.

In some embodiments, the second end of the inner body comprises threading on a surface adjacent the second opening. In some cases, devices also include a pointed tip screwed onto the second end of the inner body.

In some embodiments, a central portion of the resilient strip is spaced apart from the inner body when the outer sleeve is in its extended position and the second end of the strip of resilient material is disposed in the cavity.

In some embodiments, the outer sleeve has a hollow cylindrical shape. In some cases, devices also include a brace disposed between the inner body and the outer sleeve, the brace fixed in position relative to the outer sleeve, the brace having a generally semi-cylindrical shape with a rounded end extending outside the outer sleeve. In some cases, devices also include a connector extending through the slot, the connector fixed in position relative to the outer sleeve and abutting the strip of resilient material.

In some embodiments, the strip of resilient material comprises implant grade material.

In some embodiments, the strip of resilient material is a first strip of resilient material and the device further comprises a second strip of resilient material having a first end and a second end, the first end of the second strip of resilient material fixed in position relative to the outer sleeve; wherein the second end of the second strip of resilient material is engaged with the inner body when the outer sleeve is in its extended position and disengaged from the inner body when the outer sleeve is in its retracted position.

Some embodiments of these surgical instrumentation can provide some or all of the following advantages. A non-attached tip can provide a fail-safe disengage/reengage mechanism for the strips of resilient material that reduces the likelihood that the instrument will jam inside vertebra. A low friction hinge for low stress expansion of strips of resilient material can reduce the likelihood of requiring excessive force for activation. A slip fit of a proximal section of strips of resilient material for low friction free, manual activation can reduce the likelihood of requiring excessive force for activation. A body that is stationary with respect to the handle can reduce the risk of patient injury while providing higher security and comfort for the surgeon. A distal tip design can allow for two strips of resilient material within a small cannula size (e.g., ø<4 mm) that allows the use of the instrument through a pedicle. A manual, direct force, squeeze handle activation with low friction can provide direct, tactile feedback for distal resilient blade expansion and allows for the assessment of tissue quality. A locking nut for locking instrument in active, expanded position can enable x-ray imaging with surgeon out of x-ray field. The device can include stress-relieving braces for the strips of resilient material that can reduce the likelihood the strips break. This approach can increase the fatigue strength of the strips, allowing for use of the instrument bi-pedicularly (e.g., the instrument can be inserted through one pedicle of a vertebrae, activated, de-activated, withdrawn, inserted through the other pedicle of the same vertebrae, activated, de-activated, and withdrawn) and on multiple levels (e.g., the instrument can be inserted into one vertebrae, activated, de-activated, withdrawn, inserted into another vertebrae, activated, de-activated, and withdrawn) without strip breakage. In contrast, once a balloon-based device is activated and the balloon deployed, it is difficult or impossible to recover the balloon back into its initial position to reset the device. This approach also allows for easy replacement of the strips of resilient material.

The stripes of resilient material disengage and automatically reengage during surgical use, therefore reducing the risk of instrument breakage or instrument jamming with tissue. This feature reduces the likelihood of excessive rotational force breaking strips of resilient material; of tissue jamming between strips of resilient material preventing removal of the instrument out of surgical site; of excessive manual force being required to expand/deform stripes of resilient material; and of material stress points in strips of resilient material.

The details of one or more embodiments of these devices and methods are set forth in the accompanying drawings and the description below. Other features, objects, and advantages of these devices and methods will be apparent from the description and drawings, and from the claims.

DESCRIPTION OF DRAWINGS

Like reference symbols in the various drawings indicate like elements.

DETAILED DESCRIPTION

Figure 1A:
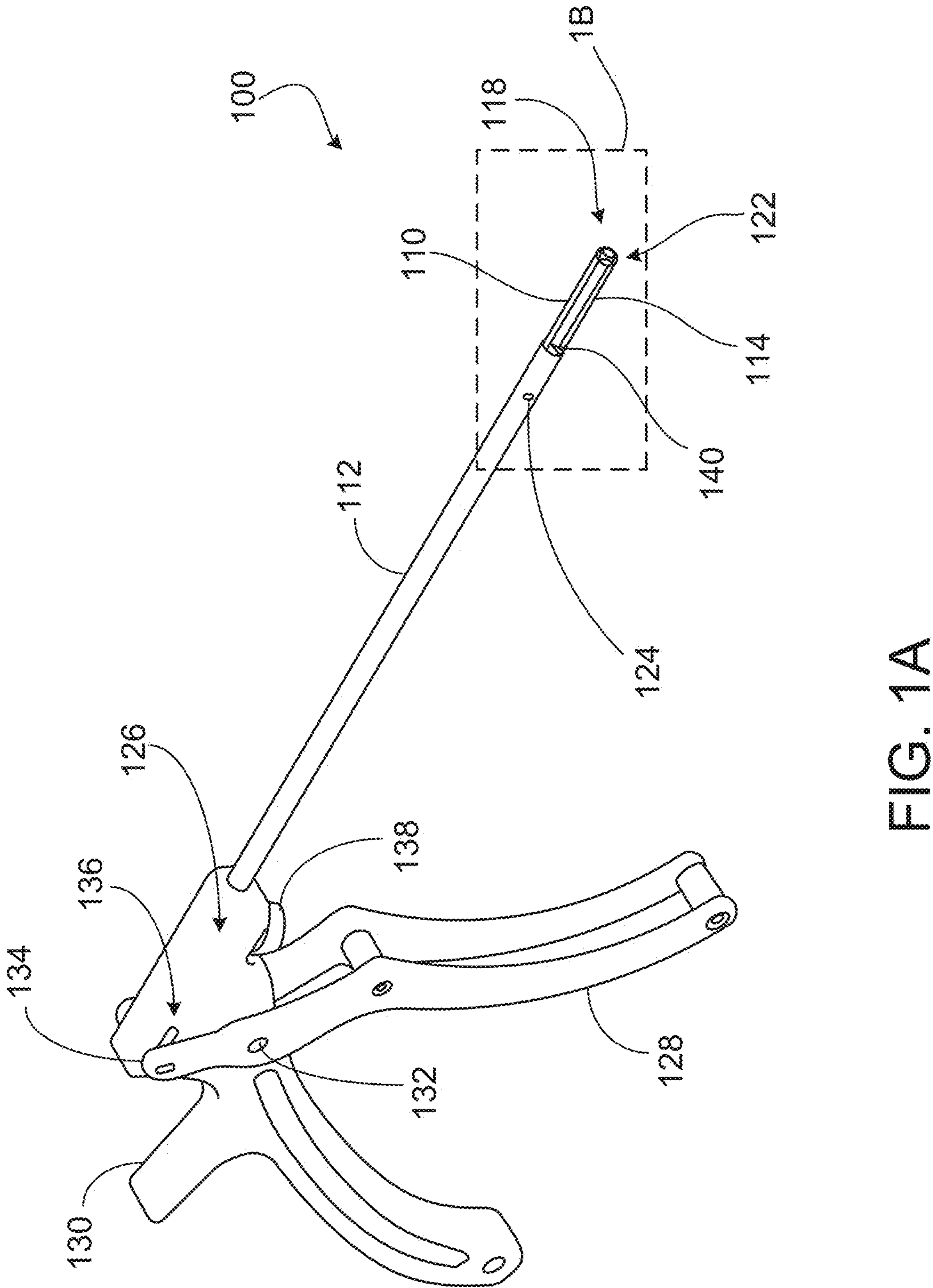
FIG. 1A is a perspective view of a device for displacing structures in a body.
Figure 1B:
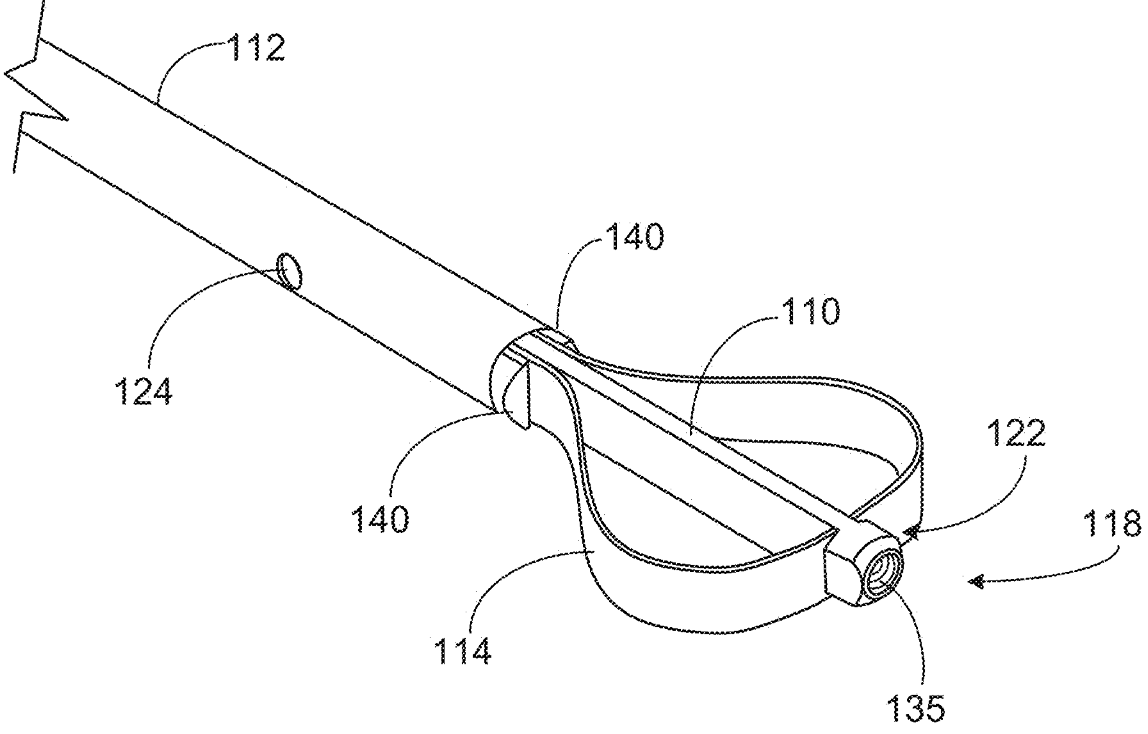
FIGS. 1B and 1C are detailed views of different portions of the device of FIG. 1A.

This specification describes systems and methods for transversely displacing structures in the body. These systems and methods can be used for restoring bone, particularly for performing bone alignment and displacement in the spine of a human or other animal.

Some systems include an instrument with an elongated body that is connected or affixed to a handle of the instrument. The elongated body is partially positioned within a sleeve that is movable relative to the body. One or more substantially planar or flat strips of resilient material are positioned partially within the sleeve and are fixed in position relative to the sleeve. In operation, the strips of resilient material releasably engage the end of the elongated body that is away from the handle of the instrument.

In its fully relaxed position when the instrument is not activated, the strip(s) of resilient material can freely move away from and towards the planar surface of the elongated body. While displacing tissue, in its expanded state, the strips of resilient material can disengage from the end of the elongated body when encountering excess forces or when tissue pieces get lodged between the resilient blade and the planar surface of the stationary body, in order to prevent breaking of the resilient blade or to allow removal of the instrument through the access cannula. When the instrument is in its fully relaxed position, automatic reengagement of strip(s) of resilient material can occur after safety disengagement due to excessive forces or jamming with debris of strip(s) of resilient material during surgical use.

FIGS. 1A-1E show a device 100 for displacing structures in a patient's body. The device 100 has an inner body 110, an outer sleeve 112, and two strips 114 of resilient material. The inner body 110 and the outer sleeve 112 are coaxial and part of the inner body 110 is positioned within the outer sleeve 112. The inner body has a first end 116 (shown in FIG. 4) and a second end 118. The inner body 110 extends out of the outer sleeve 112 on both the distal and proximal ends. The outer sleeve 112 is movable relative to the inner body 110 between a retracted position (shown in FIG. 1A) and an extended position (shown in FIG. 1B).

The strips 114 of resilient material each have a first end 120 (shown in FIG. 6C) and a second end 122. The first end 120 of each strip 114 of resilient material is fixed in position relative to the outer sleeve 112 such that movement of the outer sleeve 112 and movement of the first end 120 of the strip of resilient material are coupled. In the device 100, a pin 124 (also shown in FIG. 6C) extends through the outer sleeve and the strips 114 of resilient material. The second end 122 of each of the strips 114 of resilient material is releasably engaged with the inner body 110 when the outer sleeve 112 is in its extended position and disengaged from the inner body 110 when the outer sleeve 112 is in its retracted position. FIG. 1A shows the strip of resilient material in the non-activated state, arranged flat against the inner body 110.

Some devices only have a single strip 114 of resilient material and some devices have more than two strips 114 of resilient material. The device 100 has strips 114 of resilient material made of implant grade material such as, for example, Nitinol, Poly Ether Ether Ketone (PEEK), Poly Ether Ketone Ketone (PEKK). Use implant grade material allows the strips 114 to be left in the body if they break off during use. The material can have elastic modulus between approximately 25 MPa and 85 MPa (e.g., approximately 45 GPa, a yield strength between approximately 70 MPa and 690 MPa, an ultimate tensile strength between approximately 895 MPa to 1900 MPa.

Figures 1C, 1D:
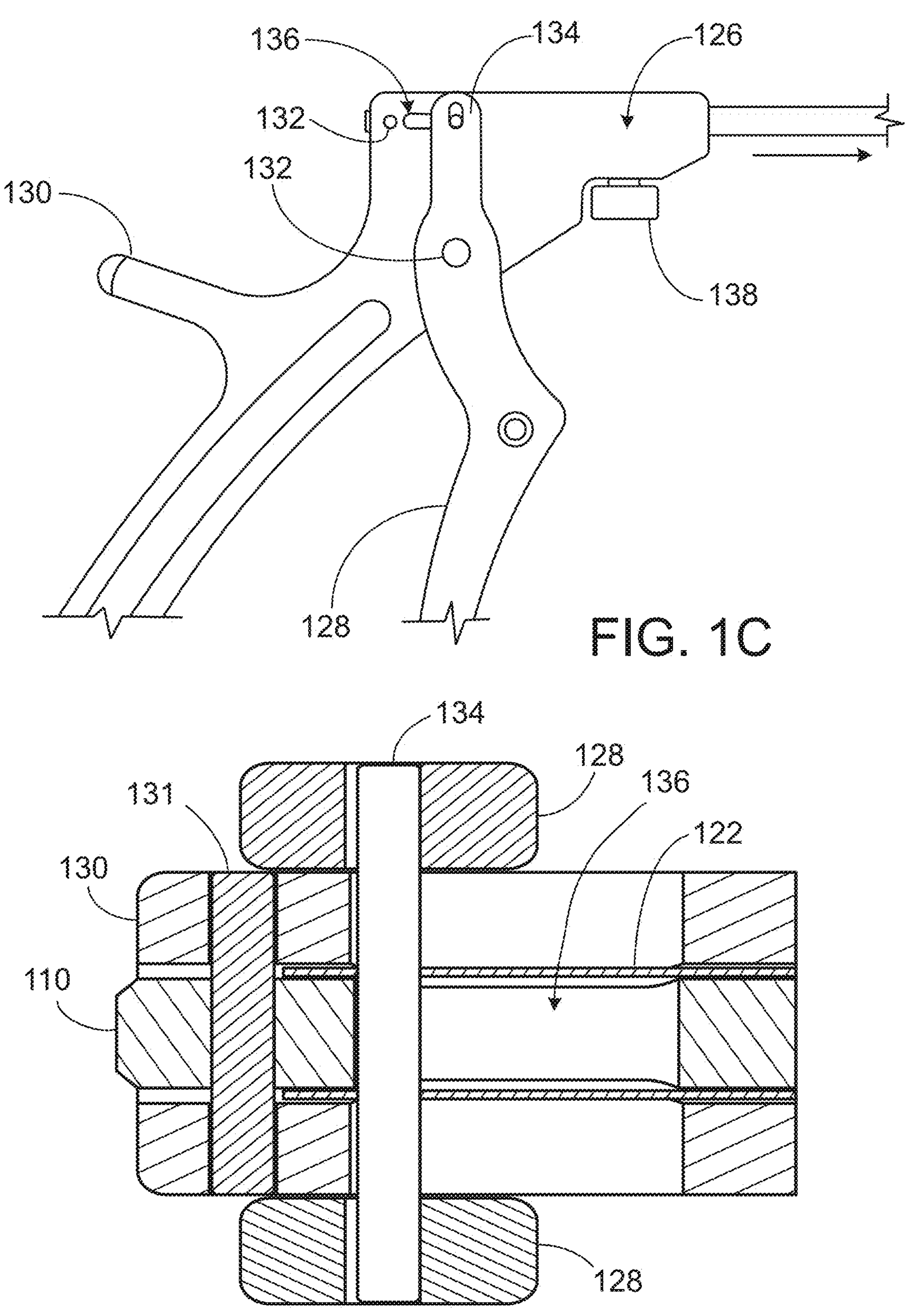
FIG. 1D is a cross-section of a portion of the device of FIG. 1A.
Figure 1E:
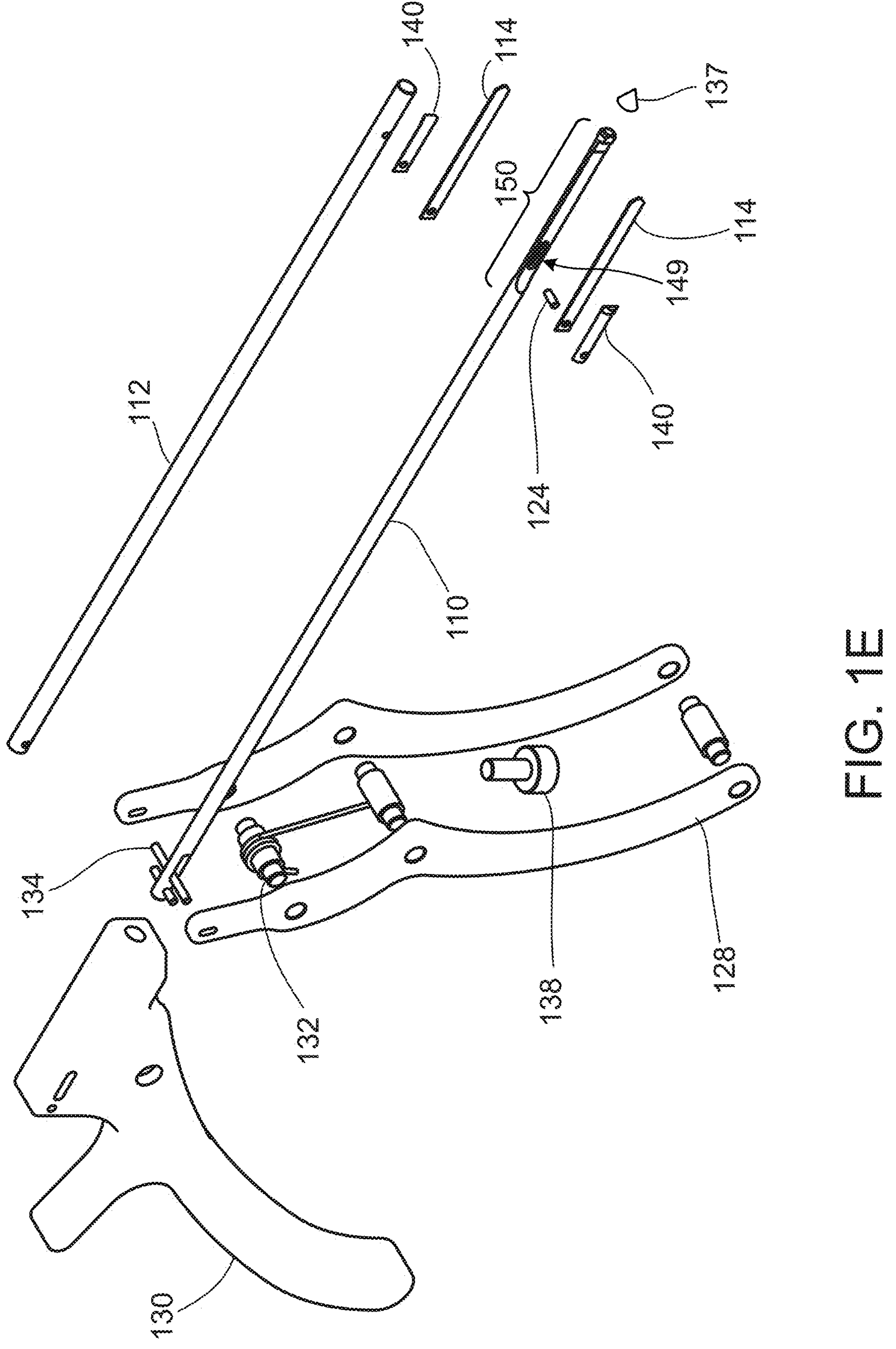
FIG. 1E is an exploded view of the device in FIG. 1A.

The device 100 also includes a handle 126 (best seen in FIG. 1C). The handle 126 has a trigger 128 attached to a base 130. The base 130 of the handle is fixed in position relative to the inner body 110. The trigger 128 is mechanically connected to the outer sleeve 112, such that the outer sleeve 112 moves from the retracted position to the extended position when the trigger 128 is activated. In FIG. 1A, the trigger 128 is not activated and the outer sleeve 112 is in its retracted position. In FIG. 1C, the trigger is activated.

Two factors help the trigger to return to its retracted position when the trigger is released. The resilient strips automatically return to their flat, planar position and therefore exert a force back through the outer sleeve onto the trigger. In addition, a torsion spring (see FIG. 1E) around pin 132 helps to bias the trigger to its retracted position.

In the device 100, the trigger 128 is attached to the base 130 by a pin 132. Another pin 134 connects the trigger 128 to the outer sleeve 112. Rotation of the trigger 128 about the pin 132 moves the pin 134 within a slot 136 defined in the base 130 and a slot 148 (see FIG. 4) defined in the inner body 110. As the pin 134 moves in the slot of the trigger, the slot in the trigger translates the rotational movement from the trigger into a linear movement of pin 134. The proximal connector pin 134 slides freely up and down in the slot 136 of the trigger 128 on both the left and right side portions of the trigger. The connector pin 134 is coupled, securely fixed to the proximal end of the outer sleeve through the hole 142 and also freely moves within the slot of the handle and the proximal slot of the inner body.

For example, activation of the trigger 128 by pulling a grip portion of the trigger 128 towards the base 130 rotates the trigger 128 about the pin 132. The rotation causes the pin 134 to move forward (to the right in FIG. 1C) and the outer sleeve to move to its extended position. Some devices use other approaches to coupling the trigger 128 to the outer sleeve 112. However, this approach's direct mechanical connection provides tactile feedback to medical personnel performing procedures using the device 100. For example, a surgeon performing a kyphoplasty using the device 100 can gauge the stage of fracture healing, the consistency of the bone (e.g., hard bone or soft bone), or the stage of osteoporosis within the vertebral body. In case of soft (i.e., highly osteoporotic) bone, the surgeon will likely decide to insert more material/PMMA/allograft implant to better stabilize the fracture or even possibly proactively treat adjacent levels.

The second end 118 of the inner body 110 also comprises threading 135 on a surface adjacent the second opening. A tip (e.g., a trocar tip) can be screwed onto the second end 118 of the inner body 110 using threading 135. Some devices use other approaches to attaching the tip to the second end 118 of the inner body 110 (e.g., a press fit, a shrink fit, gluing, pinning, or snapping). The tip may be pointed. The pointed tip allows the device 100 to create a channel into the body of a patient. This eliminates the need of a separate drill that is currently used when the surgeon creates the cavity with a balloon.

The second end 118 of the inner body 110 is chamfered to provide a symmetrical sloping edge. The chamfered second end of 118 of the inner body 110 allows for the second end of the inner body 110 to be pushed into the tissue. During tests, the chamfered second end 118 of the inner body 110 was sufficient for the instrument to be pushed into the vertebral body without having a sharper tip attached to the second end 118 of the inner body 110.

The handle also has a locking nut 138 operable to lock the outer sleeve 112 in position (e.g., in its extended position, in its retracted position, or in a position between its extended and retracted positions). The locking nut 138 may be threaded so that it can be rotated to lock the outer sleeve 112. Alternatively, the locking nut may be pressed into a locking position by the user to lock the outer sleeve 112. Locking the outer sleeve 112 also locks the trigger 128.

Figures 2A, 2B, 3, 4:
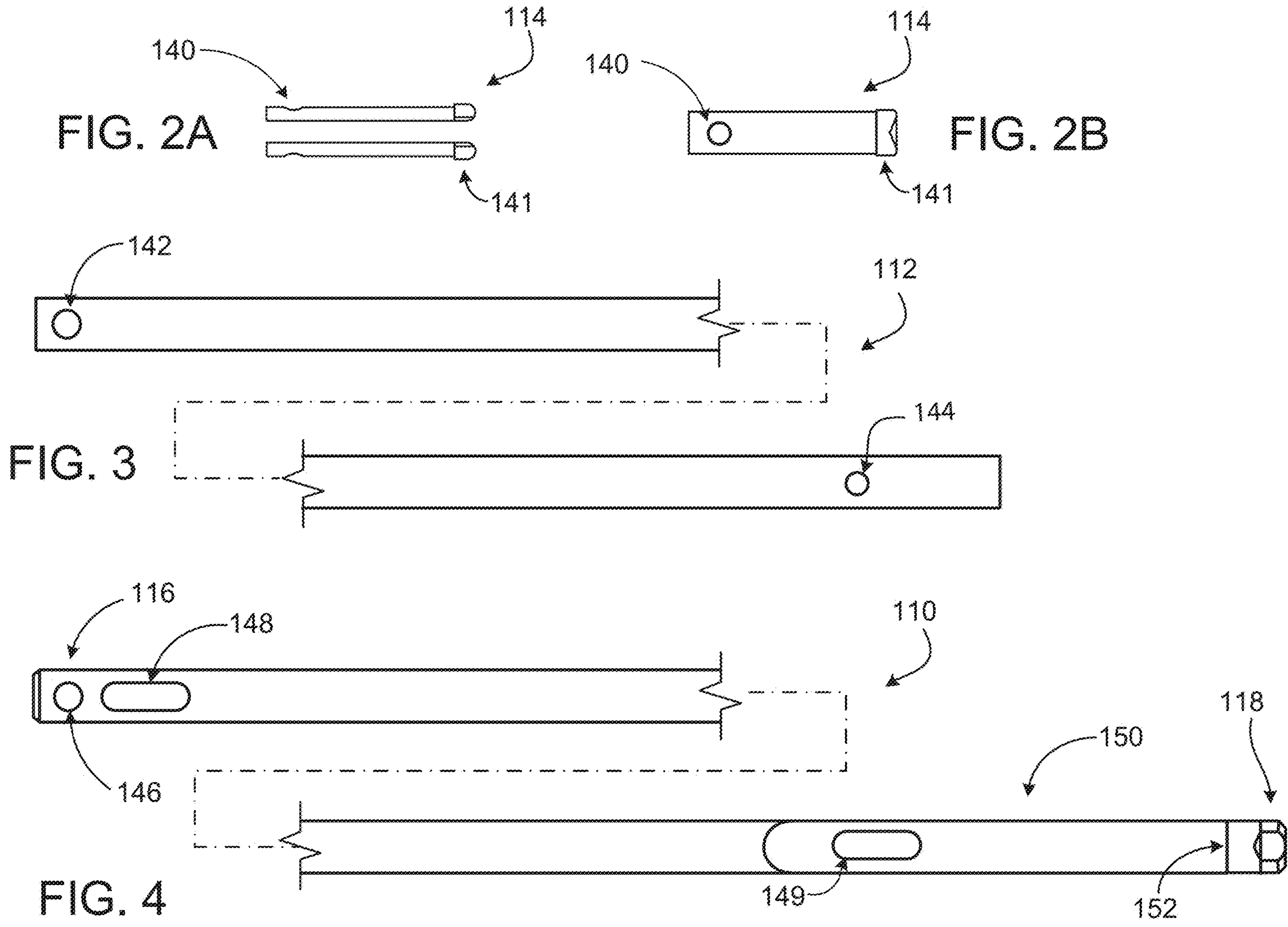
FIGS. 2A and 2B are, respectively, a side view and a top view of a brace that can be used in a device for displacing structures in a body.
FIG. 3 is a side view of an outer sleeve that can be used in a device for displacing structures in a body.
FIG. 4 is a side view of an inner body that can be used in a device for displacing structures in a body.

The outer sleeve 112 has a substantially hollow cylindrical shape. Two braces 140 are positioned within the outer sleeve 112 between the outer sleeve 112 and the strips 114 of resilient material. The braces 140 have a generally semi-cylindrical shape with a rounded end and are disposed between the inner body 110 and the outer sleeve 112. The braces 140 are fixed in position relative to the outer sleeve 112 by the pin 124. In some devices, the braces are welded or glued to the outer sleeve. The braces 140 partially extend outside the outer sleeve 112 and relieve stress on the strips 114 of resilient material when the strips 114 are flexed or bowed. The braces 140 are configured to reduce breakage of the strips 114 of resilient material. During multiple activations of the instrument 100, the braces increase the fatigue strength/resistance of the strips to allow for bi-pedicular and multi-level or even multi-patient use. The first ends 120 of the strips 114 of resilient material are disposed between the inner body 110 and the braces 140. A hole on the proximal side of the strips 114 of resilient material receives the pin 124. With this approach, the strip cannot be replaced but is secured in place and will not be able to fall out accidentally during surgery. In some devices, the strips 114 of resilient material abut to the pin 124. With this approach, strips 114 of resilient material can easily be replaced, FIGS. 2A and 2B shows one of the braces 140. The brace 140 includes a rounded tip 141. The brace 140 defines an opening 143 for receiving the pin 124 (shown in FIG. 1A) that couples the outer sleeve 112 with the strips 114 of resilient material and the braces 140. The braces 140 are made of stainless steel. In some devices, the braces are made of other materials such as, for example, plastic or aluminum. In addition to reducing the material stress on the strip and increasing the fatigue life of the strips, the braces 140 also provide a planar surface for the proximal end of the strips 114 on one side. The other planar surface on the other side is provided by the recessed portion 150 of the inner body 110. The planar surfaces are spaced apart to allow for a friction free movement of the strips along the recessed portion 150 of the inner body. The space between the two planar surfaces is slightly larger than the thickness of the strip.

FIG. 3 is a side view of the outer sleeve 112. The outer sleeve 112 defines an opening 142 sized to receive the pin 134 that couples the outer sleeve 112 with the trigger 128 (shown in FIG. 1A). The outer sleeve 112 also defines an opening 144 sized to receive the pin 124 that couples the outer sleeve 112 with the strips 114 of resilient material and the braces 140 (shown in FIG. 1A). The outer sleeve 112 is hollow and is sized to receive the first ends 120 of the strips 114 of resilient material, the braces 140, and the inner body 110. In a prototype, the outer diameter of the outer sleeve is ø 3.94 mm (less than ø 4.00 mm) and the inner diameter of the outer sleeve at the distal tip is ø 3.6 mm for a length of 15 mm. The rest of the inner diameter of the outer sleeve is ø 3.45 mm. The outer sleeve 112 of the device 100 is generally cylindrical but some devices have other cross-sections (e.g., a triangular cross section or a square cross section).

FIG. 4 is a side view of the inner body 110. The first end 116 of the inner body 110 defines an opening 146 and a slot 148. The opening 146 is sized to receive a pin (not shown) that fixes the inner body 110 to the base 130 of the handle 126 such that the second end 118 of the inner body 110 is fixed in position relative to the base 130 of the handle 126. When the device 100 is assembled, the slot 148 of the inner body 110 is aligned with the slot 136 in the base 130 of the handle 126. The slot 148 is sized to receive the pin 132 that connects the trigger 128 to the outer sleeve 112. The slot 148 has a length that is equal to or greater than the displacement of the outer sleeve 112 during operation of the device 100. When the trigger 128 is not activated, the pin 132 is positioned at the end of the slot 148 towards the first end 116 of the inner body 110. When the trigger is fully activated, the pin 132 is positioned at the end of the slot 148 towards the second end 118 of the inner body 110. This configuration allows the pin 132 to move within the slot 148 without applying substantial pressure to the inner body 110.

The inner body 110 has a recessed portion 150 which receive the strips 114 of resilient material when the device 100 is assembled and the outer sleeve 112 is in its retracted position. The second end 118 of the inner body 110 defines a cavity 152 that is aligned with the recessed portion 150 (see also FIG. 1E). In the inner body 110, the cavity 152 extends through the second end 118. These features of the inner body can be formed by machining a blank for the inner body to form the recessed portion 150 and then drilling from the distal end until the cavity 152 intersects the recessed portion 150. The cavity 152 interacts with the strips 114 of resilient material to act as a low friction or friction free hinge when the outer sleeve 112 is moved from its retracted position to its extended position during operation.

Figure 5A:
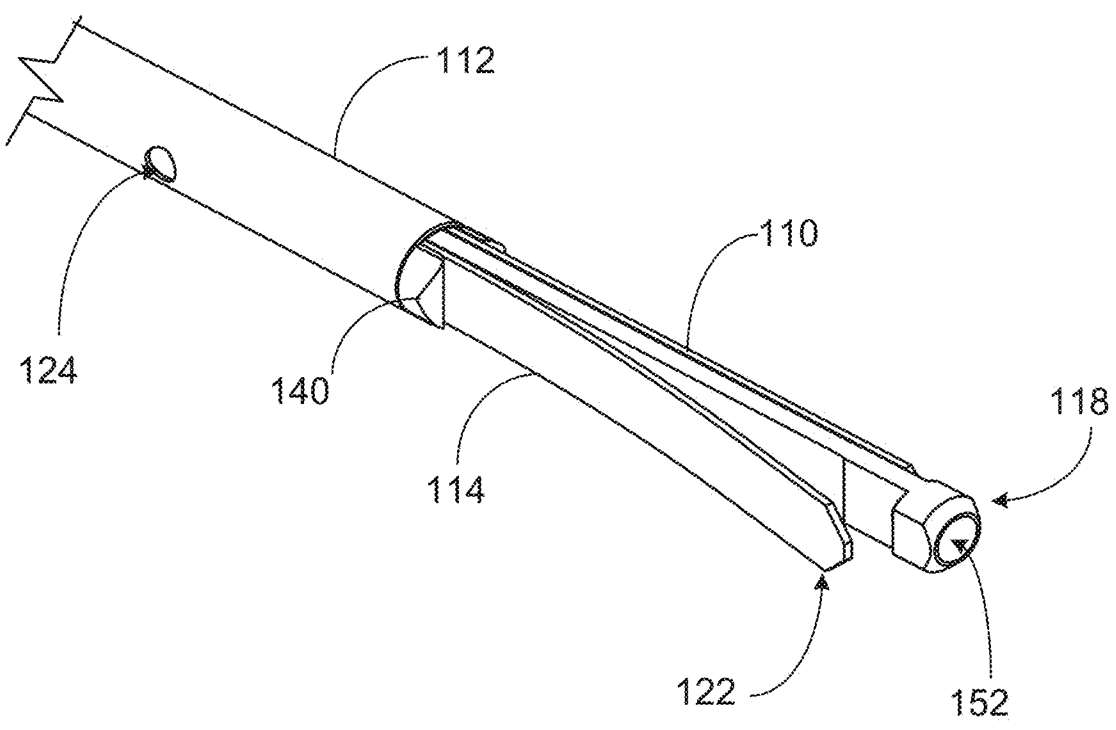
FIGS. 5A, 5B, 5C, and 5D are, respectively, a perspective view, a side view, a cross-sectional view, and a top view of one end of the device in FIG. 1A.
Figure 5B:
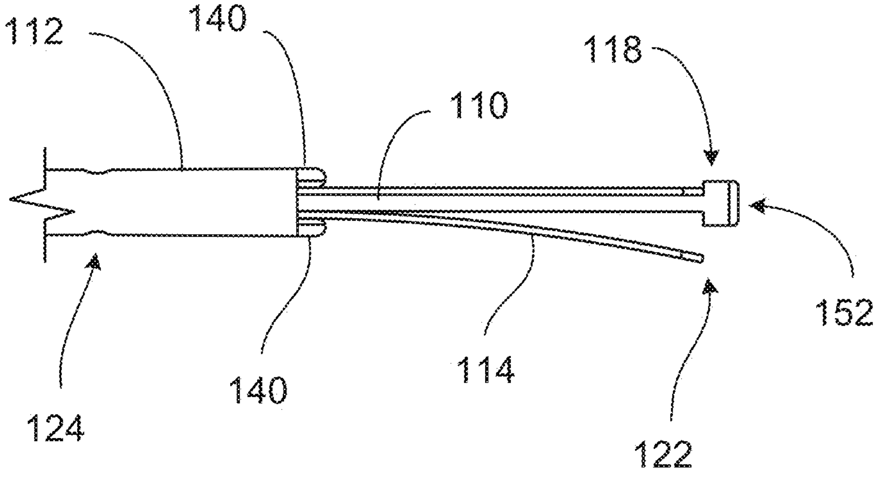

FIGS. 5A-5D show the relationship between the inner body 110 and the strips 114 of resilient material that provides this hinge functionality in additional detail. FIGS. 5A and 5B show a portion of the device 100 with the outer sleeve 112 in its retracted position (i.e., device 100 is not activated). When the outer sleeve 112 is in its retracted position, the second ends 122 of the strips 114 of resilient material are flush with or slightly outside the cavity 152. This positioning allows the strips 114 of resilient material to move outward and, more importantly, inward with little or no contact with the portion of the second end 118 of the inner body 110 that defines the cavity 152. The significance of this feature is discussed in more detail in the description of FIGS. 6A-6C.

Figure 5C:
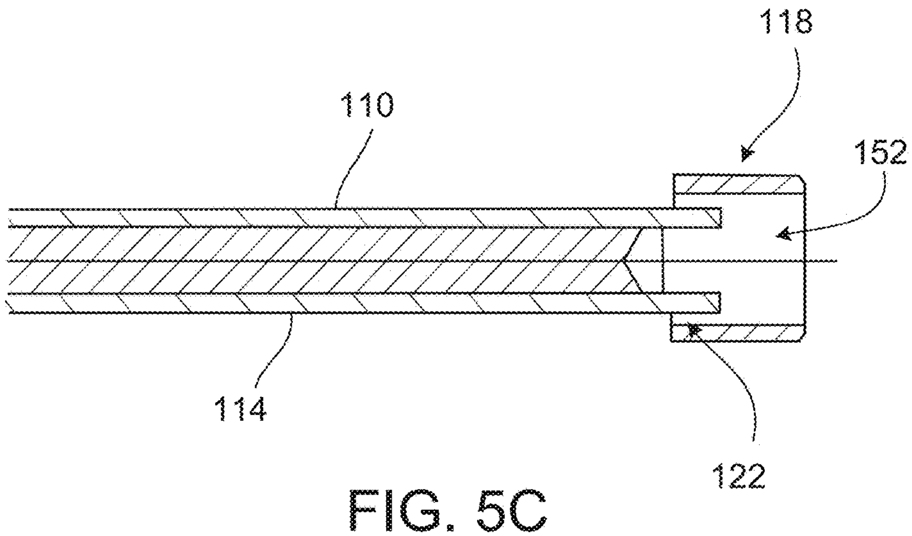
Figure 5D:
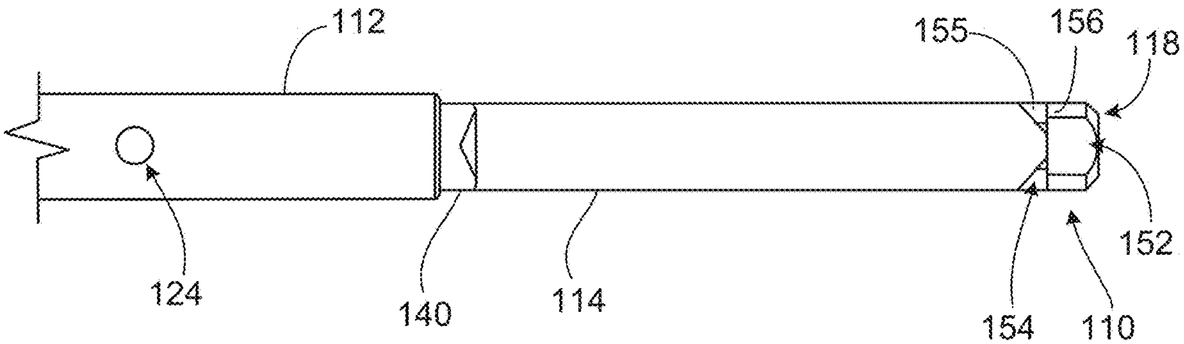

FIGS. 5C and 5D show the relationship between the strips 114 of resilient material and the inner body 110 just after the trigger 128 is activated. As the outer sleeve 112 starts to move from its retracted position to its extended position, the strips 114 of resilient material move towards the second end 118 of the inner body. The second ends 122 of the strips 114 of resilient material are shaped such that a portion of each of the second ends 122 enters the cavity 152 before the strips 114 of resilient material contact the second end 118 of the inner body 110. Contact between angled faces of the tapered end 154 and the walls 156 of the second end 118 of the inner body 110 holds the second ends 122 of the strips 114 of resilient material in place relative to the inner body 110 as the outer sleeve 112 and the first ends 120 of the strips 114 of resilient material continue to move toward the second end 118 of the inner body 110.

In the device 100, the second end 122 of each of the strips 114 of resilient material has a tapered shape as shown in FIG. 5D. In some devices, the second ends 122 of the strips 114 of resilient material have different shapes such as, for example, a rectangular tab sized to enter the cavity 152. In some devices, the second end 122 of each of the strips 114 is flat. With this approach, the strips 114 do not enter the cavity 152 but rather push against the wall 156. With this option, lower rotational forces disengage the second ends 122 of the strips 114 from the inner body 110.

Figure 6A:
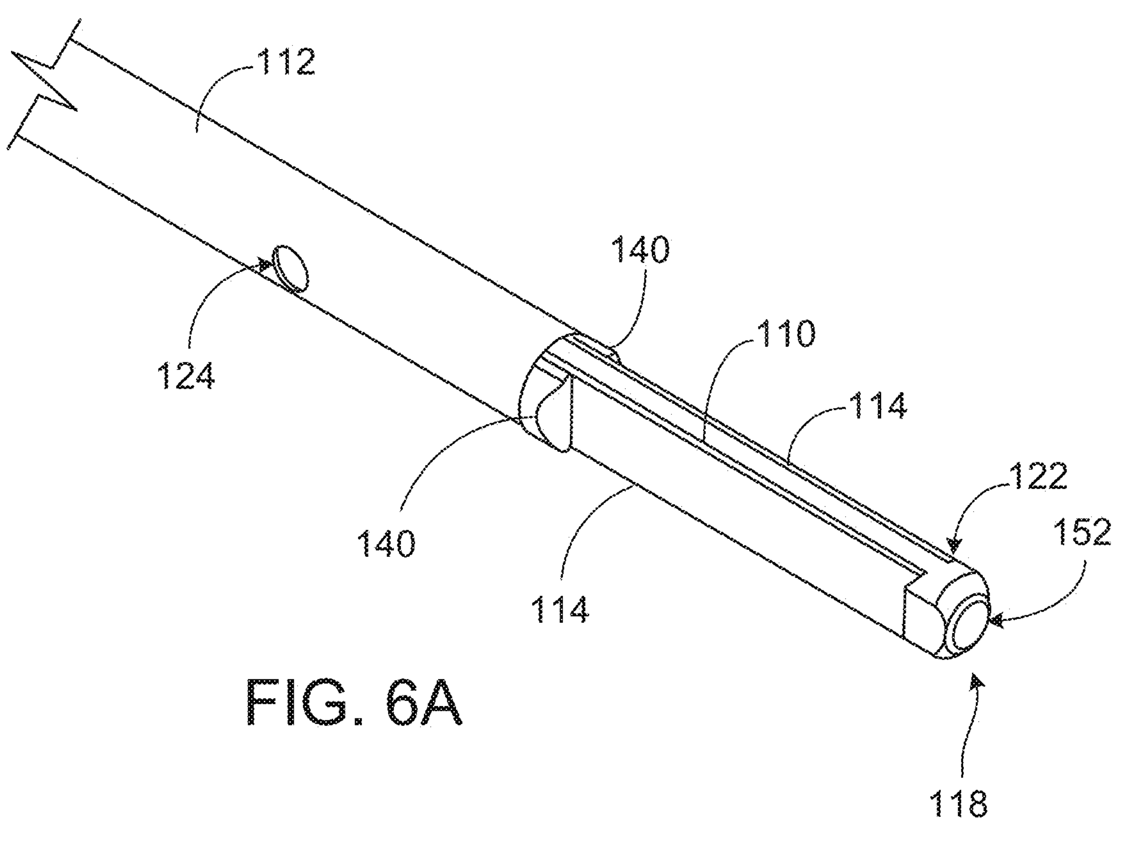
FIG. 6A is a perspective view of one end of the device in FIG. 1A in a non-activated state.
Figure 6B:
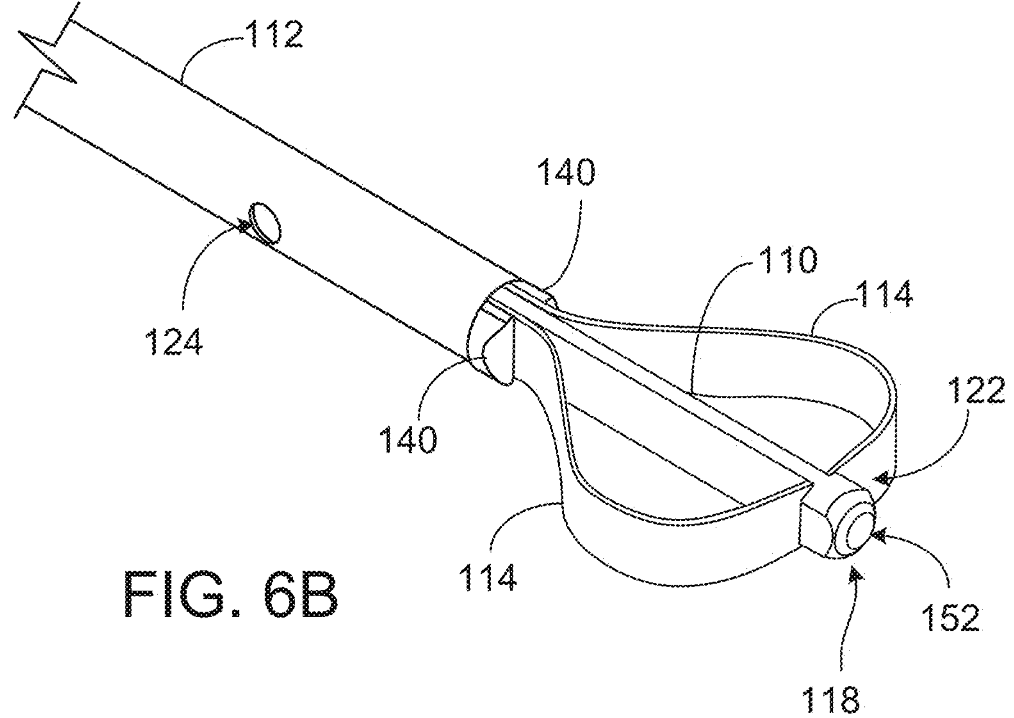
FIGS. 6B and 6C are, respectively, a perspective view and a cross-sectional view of that end of the device in FIG. 1A in an activated state.
Figure 6C:
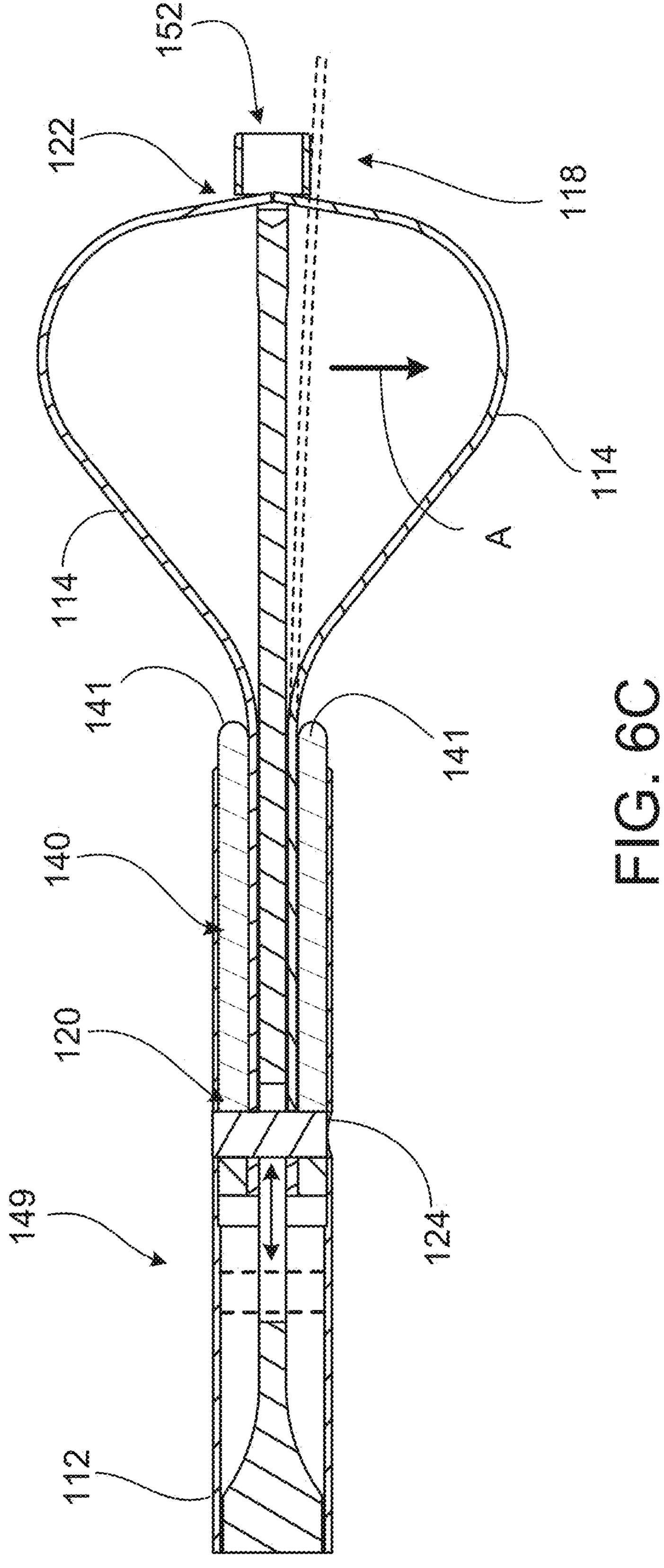

FIGS. 6A-6C illustrate the operation of the device 100 with a focus on the tip of the device that would be inserted into a patient. In FIG. 6A, the device is not activated. The outer sleeve 112 is in its retracted position relative to the inner body 110. As previously discussed, the pin 124 fixes the position of the strips 114 of resilient material and the braces 140 with respect to the outer sleeve 112 so the strips 114 of resilient material and the braces 140 are also in their retracted positions. The second ends 122 of the strips 114 of resilient material are outside the cavity 152 defined by the second end 118 of the inner body 110.

FIGS. 6B and 6C are, respectively, a perspective view and a cross-sectional view of one end of the device in FIG. 1A in an activated state. The device is activated by moving the outer sleeve 112 towards the second end 118 of the inner body 110. As shown in FIG. 6C, the pin 124 extends through the outer sleeve 112, the braces 140, and the strips 114 of resilient material so they are fixed in position relative to each other. The pin 124 extends through a distal slot (i.e., the slot 149) in the inner body 110. The slot 149 limits the distance that the pin 124, the outer sleeve 112, the braces 140, and the strips 114 of resilient material can move relative to the inner body 110. Movement of the outer sleeve 112 moves the pin 124 within the slot 149 defined by the inner body 110 between the retracted position indicated by the dashed rectangle and the extended position. Moving the outer sleeve 112 and the pin 124 towards the second end 118 of the inner body 110 also moves the braces 140 and the strips 114 of resilient material towards the second end 118 of the inner body 110.

After a short distance, the second ends 122 of the strips 114 of resilient material enter the cavity 152 and engage the second end 118 of the inner body 110 as shown in FIGS. 5C and 5D. As movement of the outer sleeve 112 towards the second end 118 of the inner body 110 continues, contact between the angled faces 155 of the tapered end 154 and the walls 156 of the second end 118 of the inner body 110 stops axial movement of the second ends 122 of the strips 114 of resilient material relative to the inner body 110. The second ends 122 of the strips 114 of resilient material pivot within the cavity 152 as shown in FIG. 6C. In effect, the interaction between the second ends 122 of the strips 114 of resilient material and the second end 118 of the inner body 110 provides a low- or no-friction hinge while the strips 114 of resilient material flex outwards.

As movement of the outer sleeve 112 towards the second end 118 of the inner body 110 continues after contact stops axial movement of the second ends 122 of the strips 114 of resilient material relative to the inner body 110, the axial distance between the first ends 120 and the second ends 122 of the strips 114 of resilient material decreases. The center portions of the strips 114 of resilient material flex away from the inner body 110. The flexing of the center portions of the strips 114 of resilient material is used to displace structures in the patient's body transversely. Typically, the instrument is slightly rotated after activation and activated. This process can be repeated though a 180 degrees of rotation to create a cylindrical cavity.

The first ends 120 of the strips 114 of resilient material are positioned between the inner body 110 and the braces 140. As the strips 114 of resilient material flex away from the inner body 110, the rounded tips 141 of the braces 140 bias the bend of the strips 114 of resilient material towards a curved configuration that is lower stress than sharper angled configurations. The reduced stress on the strips 114 of resilient material at this point is anticipated reduce the likelihood that the strips 114 will break during multiple uses, therefore increasing the fatigue resistance/life of the strips 114.

During use, debris or material lodging between the strips 114 of resilient material and the inner body 110 can apply an outward force on the flexed strips 114 as indicated by arrow A in FIG. 6C. The second ends 122 of the strips 114 of resilient material are not fixed to the inner body 110 so such an outward force can disengage the strips 114 of resilient material from the cavity 152. When this occurs, the disengaged strip 114 of resilient material is biased towards the shape and position indicated by the dashed lines. Debris or material typically is dislodged from the strip 114 as this occurs. In the unlikely event that debris or material within the space being created by use of the device 100 or the bone defining the boundaries of the space keep the disengaged strip 114 of resilient material from reaching this shape and position, the instrument can be activated and deactivated as necessary to dislodge the debris or material. The feature of the second ends 122 of the strips 114 of resilient being separable from the cavity 152 is anticipated reduce the likelihood that debris or material will remain lodged between the strips 114 and base 150 and that the strips 114 will break during use so that the instrument can be safely removed from the patient without jamming. Typically, the instrument is inserted into the patient through a separate access cannula/tube.

After this disengagement occurs, the device can be returned to an operational state by deactivating the device (e.g., by releasing the trigger 128). As the outer sleeve 112 returns to its retracted position, the braces 140 and the first ends 120 of the strips 114 of resilient material move away from the second end 118 of the inner body 110. As the second end 122 of the disengaged strip 114 reaches the position where it is flush with or slightly away from the second end 118 of the inner body 110, the disengaged strip 114 will tend to resume its position in the recessed portion 150 of the inner body 110. During this step, debris or material tends to be dislodged or freed from the instrument therefore allowing the free/simple removal of the instrument from the patient. In some instances, this reset can be performed without removing the tip of the device 100 from the patient's body. Debris or material stuck between the disengaged strip 114 and the inner body can prevent the disengaged strip 114 from resuming its position in the recessed portion 150 of the inner body 110. If this occurs, it may be necessary to remove the tip of the device 100 from the patient's body to clear away the debris or material and perform the reset.

Figures 7A, 7B:
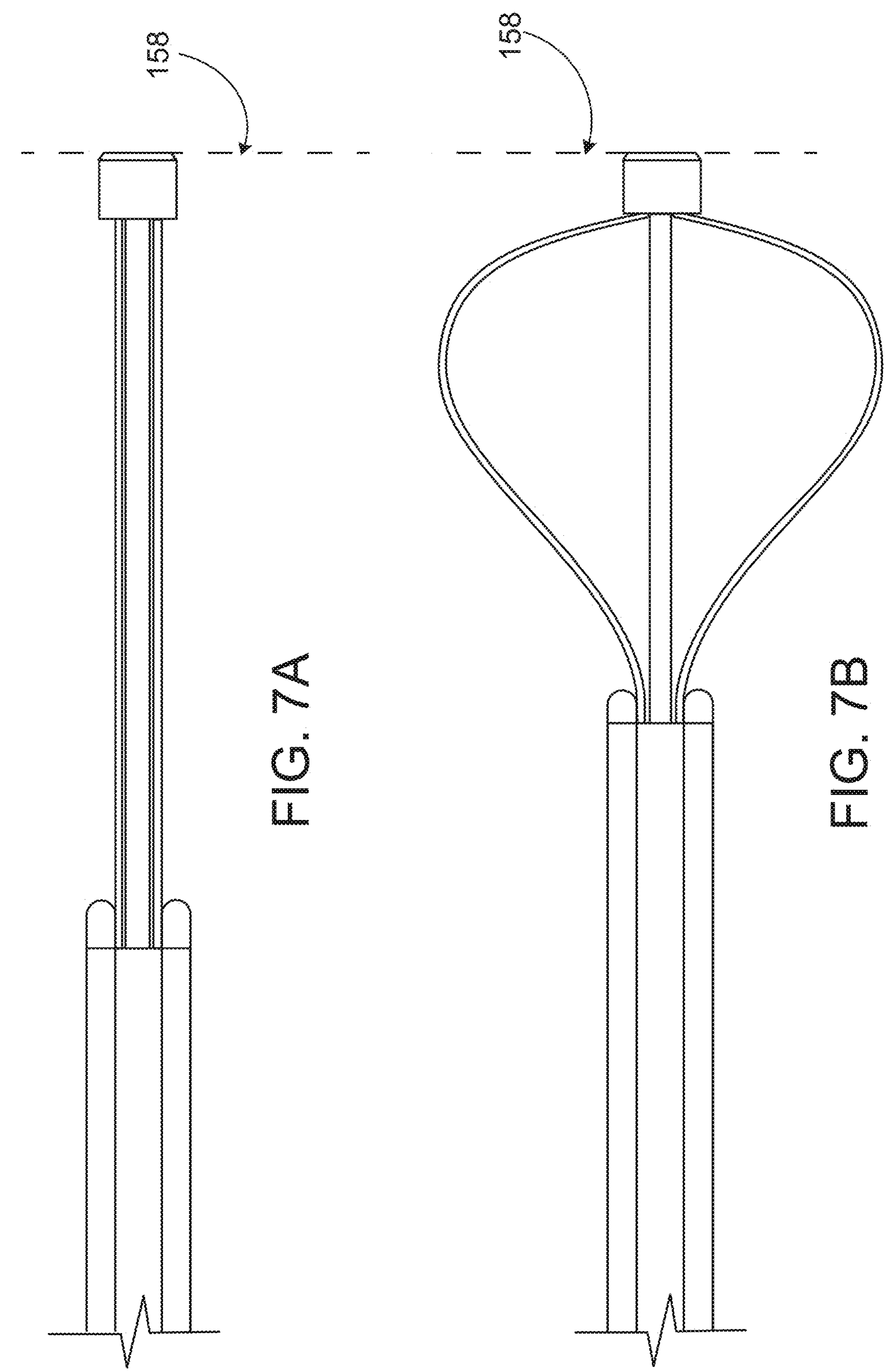
FIGS. 7A and 7B are side views of one end of the device in FIG. 1A in a non-activated state and in an activated state, respectively.

FIGS. 7A and 7B illustrate a feature provided by the fixed position of the inner body 110 relative to the handle 126. FIGS. 7A and 7B, respectively, show the device 100 before and after the trigger 128 is activated. A reference line 158 is shown on both FIGS. 7A and 7B. As the device 100 is activated the strips 114 of resilient material move from their non-activated position to their flexed position, but the second end 118 of the inner body 110 remains stationary. Most notably, the end of the inner body 110 does not move relative to the reference line 158 when in the extended position or the retracted position. This feature allows medical personnel to position the device 100 in a patient's body and operate the device without concern that the end of the device 100 will penetrate farther into the patient's body as long as the handle 126 is maintained in a fixed position. This can be clinically important in order to avoid tissue damage from the distal tip of the device. Specifically, the concern of anterior breakthrough of the vertebral body and accidental harm or damage to the anterior vessels (aorta and vena cava) is reduced. Damage to either vessel during such a surgery can easily lead to a patient's death due to rapid bleeding that cannot be stopped in time.

Figure 8:
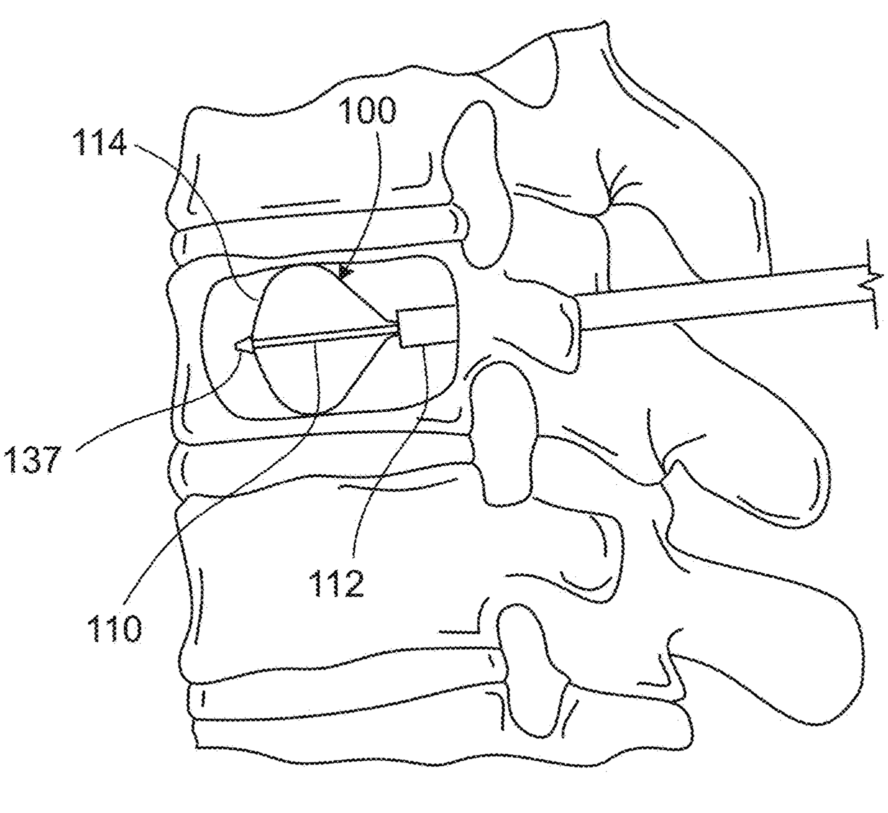
FIG. 8 shows the device of FIG. 1A in use.

FIG. 8 shows the device in use to transversely displacing structures in the spine of a patient to perform a kyphoplasty. A trocar 137 is attached to the device using the threaded section on the second end 118 of the inner body 110. The end of the device is inserted into the spine using the trocar to create a channel or pathway into the body. In some approaches, separate device is used to create a channel or pathway into the body. The trocar does not create the channel inside the vertebral body but rather is only long enough to create the channel through the pedicle. Surgeons currently use an additional drill to drill out the cancellous bone inside the vertebral body. In contrast, the trocar tip/chamfer of the current instrument allows the elimination of the drill. The device 100 is inserted with the outer sleeve 112 in its retracted position and the strips of resilient material in their non-active position. After insertion, activation of the trigger 128 (see FIG. 1A) moves the strips 114 into the flexed position to apply a force onto the tissue, bone, or other biologic material in a vertebra, to create a space in the vertebra. When the user releases the trigger 128, the strips 114 return to their non-activated position. The user can repeat activating and deactivating the trigger to create a larger space in the body, for example by rotating the device 100 or inserting the device 100 further into the body.

The elimination of the drilling step is an advantage of the current instrument over balloon-based systems. In addition, the current system eliminates the need of a pressure pump and the use of saline to inflate the balloon, therefore eliminating multiple additional steps.

Since this device provides tactile feedback, the surgeon is able to assess the health of the bone and alter his treatment accordingly. For example, she may add more material within the vertebral body. In another example, he may proactively treat adjacent vertebral bodies if tactile feedback indicates that the bone is very soft/weak. Alternatively, if the surgeon diagnoses very hard bone or a very stable fracture, the surgeon may alter his treatment with the insertion of less material and no need for adjacent level proactive treatment. In contrast to balloon-based systems, the surgeon can use a single instrument on both sides (bi-pedicular) and on multiple levels, eliminating the need of unpacking and using multiple balloons.

Figure 9:
FIG. 9 shows a device for displacing structures in a body.

A number of embodiments of the system and methods have been described. Nevertheless, it will be understood that various modifications may be made without departing from the spirit and scope of the disclosure. For example, similar devices can have more or less than two strips of resilient material. FIG. 9 shows a device 200 with a single strip 114 of resilient material. Accordingly, other embodiments are within the scope of the following claims.

What is claimed is:

1. A device for creating a cavity during spinal surgery, the device comprising:

an inner body with a first end and a second end;

an outer sleeve coaxial with the inner body, the outer sleeve movable relative to the inner body between a retracted position and an extended position;

a trigger mechanism connected to the outer sleeve and configured to apply an axial force to the outer sleeve;

a first strip of resilient material having a first end and a second end, the first end of the first strip of resilient material fixed in position relative to the outer sleeve; and a second strip of resilient material having a first end and a second end, the first end of the second strip of resilient material fixed in position relative to the outer sleeve;

wherein the second ends of the first strip of resilient material and the second strip of resilient material are releasably engaged with the inner body when the outer sleeve is in its extended position and disengaged from the inner body when the outer sleeve is in its retracted position.

2. The device of claim 1, wherein the second end of the inner body defines a cavity that is aligned with the first strip of resilient material when the outer sleeve is in its retracted position.

3. The device of claim 2, wherein the second end of the first resilient strip is outside the cavity when the outer sleeve is in its retracted position.

4. The device of claim 2, wherein the cavity extends from a first opening oriented towards the first resilient strip to a second opening oriented away from the resilient strip.

5. The device of claim 2, wherein a central portion of the first resilient strip is spaced apart from the inner body when the outer sleeve is in its extended position and the second end of the strip of resilient material is disposed in the cavity.

6. The device of claim 2, wherein the second end of the first strip of resilient material has a tapered shape.

7. The device of claim 1, further comprising a handle with a trigger, the trigger mechanically connected to the outer sleeve such that operation of the trigger moves the outer sleeve relative to the handle.

8. The device of claim 7, wherein the second end of the inner body is fixed in position relative to the handle.

9. The device of claim 1, wherein a portion of the inner body defines a slot positioned within the outer sleeve.

10. The device of claim 9, further comprising a connector extending through the slot, the connector attached to the outer sleeve and the first strip of resilient material and fixed in position relative to the outer sleeve and the strip of resilient material.

11. A device for displacing structures in a patient's body, the device comprising:

an inner body having a first end and a second end;

an outer sleeve coaxial with the inner body, the outer sleeve movable relative to the inner body between a retracted position and an extended position; and a strip of resilient material having a first end and a second end, the first end of the strip of resilient material fixed in position relative to the outer sleeve;

wherein the second end of the strip of resilient material is releasably engaged with the inner body when the outer sleeve is in its extended position and disengaged from the inner body when the outer sleeve is in its retracted position.

12. The device of claim 11, wherein the second end of the inner body defines a cavity that is aligned with the strip of resilient material when the outer sleeve is in its retracted position.

13. The device of claim 12, wherein the second end of the resilient strip is outside the cavity when the outer sleeve is in its retracted position.

14. The device of claim 12, wherein the cavity extends from a first opening oriented towards the resilient strip to a second opening oriented away from the resilient strip.

15. The device of claim 14, wherein the second end of the inner body comprises threading on a surface adjacent the second opening.

16. The device of claim 15, further comprising a pointed tip screwed onto the second end of the inner body.

17. The device of claim 12, wherein a central portion of the resilient strip is spaced apart from the inner body when the outer sleeve is in its extended position and the second end of the strip of resilient material is disposed in the cavity.

18. The device of claim 12, wherein the second end of the strip of resilient material has a tapered shape.

19. The device of claim 11, wherein the outer sleeve has a hollow cylindrical shape.

20. The device of claim 19, further comprising a brace disposed between the inner body and the outer sleeve, the brace fixed in position relative to the outer sleeve, the brace having a generally semi-cylindrical shape with a rounded end extending outside the outer sleeve.

* * * * *